United States Patent [19]

Lueken et al.

[11] Patent Number: 4,968,849
[45] Date of Patent: Nov. 6, 1990

[54] PROCESS FOR THE PREPARATION OF 2-ETHYLHEXANOL BY LIQUID-PHASE CATALYTIC HYDROGENATION OF 2-ETHYLHEXENAL, AND CATALYST

[75] Inventors: Hans-Gerd Lueken, Marl; Uwe Tanger, Bochum; Wilhelm Droste, Marl; Gernard Ludwig, Haltern; Dietmar Gubisch, Essen, all of Fed. Rep. of Germany

[73] Assignee: Huels Aktiengesellschaft, Marl, Fed. Rep. of Germany

[21] Appl. No.: 279,078

[22] Filed: Dec. 2, 1988

[30] Foreign Application Priority Data

Feb. 5, 1988 [DE] Fed. Rep. of Germany ....... 3803464

[51] Int. Cl.$^5$ ................ C07C 29/14; C07C 31/125
[52] U.S. Cl. .................................. 568/881; 502/300
[58] Field of Search ................................ 568/881

[56] References Cited

U.S. PATENT DOCUMENTS 3,886,219  5/1975  Reich .................... 568/881
3,991,127  11/1976  Corr et al. ............. 568/881

FOREIGN PATENT DOCUMENTS 150195  8/1981  German Democratic Rep. ................. 568/881
1183637  3/1970  United Kingdom ......... 568/881

*Primary Examiner*—J. E. Evans
*Attorney, Agent, or Firm*—Oblon, Spivak, McClelland, Maier & Neustadt

[57] ABSTRACT

A process for preparing 2-ethylhexanol by the liquid-phase catalytic hydrogenation of 2-ethylhexenal and a catalyst for preforming this catalytic hydrogenation are disclosed.

8 Claims, No Drawings

PROCESS FOR THE PREPARATION OF 2-ETHYLHEXANOL BY LIQUID-PHASE CATALYTIC HYDROGENATION OF 2-ETHYLHEXENAL, AND CATALYST

BACKGROUND OF THE INVENTION

1. Field of the Invention

The present invention relates to the preparation of 2-ethylhexanol and to catalysts for its preparation.

Discussion of the Background

2-Ethylhexanol is used in large quantities as an esterification component, e.g. for the preparation of dioctyl phthalate as a plasticizer for PVC. It is prepared by the hydrogenation of 2-ethylhexenal (oxo successive product).

In this process hydrogenation can occur both in the gaseous phase (DE-AS 11 52 393) and in the liquid phase (DE-AS 19 49 296). In these processes higher catalyst loads can generally be achieved in the liquid phase due to improved dissipation of heat.

In addition to the catalyst load, the purity of the product, expressed, e.g. by its bromine number, is of great interest since the plasticizers to be prepared later must exhibit good color stability.

It is known from DE-AS 19 49 296 that the liquid-phase hydrogenation of 2-ethylhexenal with cyclic processing of the reaction product with a catalyst load of approximately 1.8/h results in a product with a bromine number ranging from 3.9 to 0.2. The catalysts used here have the drawback that despite suitable catalyst loads during hydrogenation, the result is a product that is inadequate in terms of its bromine number and whose degree of purity must be improved by subsequent distillation.

Another process is known from DE-AS 12 69 605 in which, in the liquid phase and with increased pressures and increased temperatures, 2-ethylhexenal is converted to 2-ethylhexanol over nickel and/or cobalt catalysts to which copper and/or chromium and/or manganese has been added. To these catalysts one further adds a pyro- or a polyacid in the free form and/or in the form of at least a salt of the aforementioned metals.

The drawback of this process and catalysts is the need for very high pressures (preferably from 200 to 400 bar) and higher temperatures. Moreover, the catalyst loads of approximately 0.2/h and the high bromine numbers of the product ranging from approximately 0.13 to 0.1 are negative factors for hydrogenation.

The above problems make clear that there is a need for a facile catalytic hydrogenation process which is capable of producing a 2-ethylhexanol product of exceptional purity and low bromine number.

SUMMARY OF THE INVENTION

Accordingly, one object of this invention is to provide a novel process for the catalytic hydrogenation of 2-ethylhexenal to 2-ethylhexanol.

It is another object of this invention to provide a process for the catalytic hydrogenation of 2-ethylhexenal to yield a 2-ethylhexanol product of exceptional purity.

It is another object of this invention to provide a catalytic hydrogenation process for the production of a 2-ethylhexanol product having a low bromine number.

It is another object of this invention to provide a new catalyst composition which can be used to produce a 2-ethylhexanol product of exceptional purity and which possesses a low bromine number.

The inventors have now discovered a novel process in which a high purity 2-ethylhexanol product is obtained by the liquid-phase hydrogenation of 2-ethylhexenal over a novel catalyst. This process and catalyst satisfies all of these objects of the invention set out above and other objects which will become apparent from the description of the invention given hereinbelow.

In the process of this invention, 2-ethylhexenal is hydrogenated at a temperature of from 120° C. to 180° C. under a pressure from 10 to 100 bar. The catalyst composition used contains nickel in an amount of from 15 to 0.3% by weight, copper in an amount of from 15 to 0.3% by weight, chromium in an amount of from 0.05 to 3.5% by weight, and an alkali metal component in an amount of from 0.01 to 1.6% by weight. The balance of the weight of the catalyst composition is the catalyst carrier.

DETAILED DESCRIPTION OF THE PREFERRED EMBODIMENTS

Surprisingly it has been found that the hydrogenation of 2-ethylhexenal with high catalyst loads and under increased pressure and increased temperature yields a product of exceptional purity with low bromine numbers if the reaction is carried out on supported catalysts which contain copper and nickel as primary metal components, chromium as a stabilizer and an alkali component. The alkali component is preferably added to the catalyst as alkali dichromate, instead of acid additions such as pyro- or polyacids.

An unexpected, important technical advance of the invention is the facts that (1) the addition of alkali dichromates to the catalyst does not retard the reaction rate, but rather an improved product quality, expressed by bromine number, is obtained and (2) the reaction also takes place at comparatively low pressures.

The reaction is carried out at temperatures ranging from 120° to 180° C., preferably from 140° to 160° C., in particular from 145° to 155° C., and at pressures ranging from 10 to 100 bar, preferably from 20 to 50 bar, in particular from 30 to 40 bar. With the process of the invention catalyst loads ranging from 2 to 7/h are achieved and a very pure 2-ethylhexanol product having bromine numbers ranging from 0.1 to 0.01 is obtained.

The primary active components of the catalyst composition are copper and nickel which are each present in a concentration ranging from 15 to 0.3% by weight, based on the total catalyst composition mass. Preferably 0.05 to 3.5% by weight of chromium, and 0.01 to 1.6% by weight, preferably 0.02 to 1.2% by weight, of an alkali metal, added to the catalyst in the form of alkali dichromate, are added to the catalyst composition as the activator. Preferably sodium dichromate is used as an alkali dichromate. Preferably $SiO_2$ and $Al_2O_3$ are used as the catalyst carrier.

The active components of the catalyst can be distributed both homogeneously and in the form of a surface layer on the catalyst carriers.

The catalyst may be prepared by spray impregnation. If the catalyst is to contain a homogeneous distribution of the active components in the carrier, a solution is prepared that contains the active components in the form of metal salts and that corresponds somewhat to the 0.8-fold volume of the pore volume of a supporting material introduced to the coating drum. The metal salt solution, whose metal content corresponds to the desired loading of the carrier, is then sprayed on the carrier at room temperature, whereby the metal salt solution penetrates the carrier and the pore volumes of the carrier corresponding to the volume of the solution that was sprayed on is saturated.

If a surface-layer impregnated catalyst is desired, a metal salt solution is sprayed on a preheated carrier and then the carrier is heated during the spraying process. Then the metal salts crystallize into a layer whose thickness is dependent e.g. on the temperature of the carrier. For example, suitable temperatures range from 90° C. to 100° C. Prior to use, the catalyst is reduced with hydrogen.

Other features of this invention will become apparent in the course of the following descriptions of exemplary embodiments which are given for illustration of the invention and are not intended to be limiting thereof.

EXAMPLE 1

An impregnation solution is prepared from 37 g of a copper nitrate ·3H$_2$O, 857.2 g Ni(NO$_3$)$_2$ solution which is added to 14% Ni, 5.7 g of sodium dichromate ·2H$_2$O and 1.4 g of 65% nitric acid in water and dissolved. After filtration, the yield is 4,336 g of solution following addition of water. The aqueous metal salt solution is sprayed onto 1,899 g of SiO$_2$ beads at a carrier temperature of 98° C.

The moist carrier that is loaded with metal salt is dried at 110° C. and calcined at 350° C. The thickness of the surface layer is 0.24 mm. The catalyst contains 0.3% of copper, 4.5% of nickel, 0.07% of chromium and 0.03% of sodium.

The catalyst (90 g) in an isothermal tube reactor is then reduced at 200° C. with hydrogen, and to obtain a catalyst in a state of equilibrium, 0.5 liter of 2-ethylhexenal per hour are passed over the catalyst over a period of 48 hours at a temperature of 150° C. and a pressure of 40 bar. The catalyst activity in the cyclic process is then determined. To the treated catalyst, 2-ethylhexanol and crude 2-ethylhexenal are added in a ratio of 3:1 under the aforementioned temperature and pressure conditions.

The cross-sectional load of liquid material is 36 m$^3$/m$^2$/h The speed at which 2-ethylhexanol is formed is observed over a period of 6 hours. A LHSV (liquid hourly space velocity) value of 2.1/h is calculated for a 99.9% conversion. The bromine number of the 2-ethylhexanol product is 0.054.

EXAMPLE 2

An impregnating solution is prepared from 137 g of copper nitrate ·6H$_2$O, 199 g of copper nitrate ·3H$_2$O, 11.2 g of sodium dichromate ·2H$_2$O and 2.8 g of 65% nitric acid which are dissolved in water to give a metal salt solution having a volume of 928 cm$^3$. The solution is sprayed onto 1,744 g of Al$_2$O$_3$ granules at room temperature. Drying and calcining (at 450° C.) is preformed as in Example 1. The calcined catalyst contains the active components distributed homogeneously in the carrier. The metal content includes 3% copper, 1.3% nickel, 0.26% chromium and 0.11% sodium. From the data derived from the activity test according to Example 1, for a 99.9% conversion, a LHSV of 3.3/h is calculated. The bromine number of the 2-ethylhexanol product is 0.04.

EXAMPLE 3

A catalyst containing 6.5% copper, 3.1% nickel, 0.6% chromium, and 0.24% sodium is prepared and tested in the same manner as in Example 2. For a 99.9% conversion a LHSV of 6.8/h is calculated. The bromine number of the 2-ethylhexanol product is 0.018.

EXAMPLE 4

A catalyst containing 5.3% copper, 5.4% nickel, 2.5% chromium, and 1.1% sodium is prepared and tested in the same manner as in Example 1. For a 99.9% conversion a LHSV of 1.2/h is calculated. The bromine number of the 2-ethylhexanol product is 0.055.

COMPARISON EXAMPLE

A catalyst containing 5.8% copper, 5.6% nickel, 2.9% chromium is prepared and treated in the same manner as in Example 1. For a 99.9% conversion a LHSV of 1.1/h is calculated. The bromine number of the product is 0.15.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A process for preparing 2-ethylhexanol from 2-ethylhexenal, comprising:
    (i) hydrogenating 2-ethylhexenal in the liquid phase at a temperature of from 120° to 180° C. and under a pressure of from 10 to 100 bars over a catalyst composition which comprises 15 to 0.3% by weight of nickel, 15 to 0.3% by weight of copper, 0.05 to 3.5% by weight of chromium, and from 0.01 to 1.6% by weight of an alkali metal component, wherein said alkali metal component s added to said catalyst composition as a dichromate salt, the balance of said catalyst composition being a catalyst support; and
    (ii) obtaining 2-ethylhexanol.

2. The process of claim 1, comprising using a temperature from 140° to 160° C.

3. The process of claim 1, comprising using a temperature from 145° to 155° C.

4. The process of claim 1, comprising using a pressure from 20 to 50 bars.

5. The process of claim 1, comprising using a pressure from 30 to 40 bars.

6. The process of claim 1, wherein said support is SiO$_2$ or Al$_2$O$_3$.

7. The process of claim 1, wherein said nickel, copper, chromium and alkali metal component are distributed homogeneously in said catalyst support.

8. The process of claim 1, wherein said nickel, copper, chromium and alkali metal component are distributed on the surface of said catalyst support.

* * * * *

UNITED STATES PATENT AND TRADEMARK OFFICE
CERTIFICATE OF CORRECTION

PATENT NO. : 4,968,849
DATED : NOVEMBER 6, 1990
INVENTOR(S) : HANS-GERD LUEKEN ET AL.

It is certified that error appears in the above-identified patent and that said Letters Patent is hereby corrected as shown below:

On the title page item [75] Inventors: Please delete "Gernard Ludwig" and insert --Gerhard Ludwig--.

Signed and Sealed this

Fifth Day of May, 1992

*Attest:*

DOUGLAS B. COMER

*Attesting Officer*   *Acting Commissioner of Patents and Trademarks*